United States Patent [19]

Staub et al.

[11] 4,014,342
[45] Mar. 29, 1977

[54] VITREOUS CUTTER

[75] Inventors: David Edward Staub, Clearwater; Carl Leroy Foltz, Holiday; Raymond Walter Simmons, Pinellas Park, all of Fla.

[73] Assignee: Concept, Inc., Clearwater, Fla.

[22] Filed: Apr. 11, 1975

[21] Appl. No.: 567,087

[52] U.S. Cl. .............................................. 128/305.1
[51] Int. Cl.² ......................................... A61B 17/32
[58] Field of Search ............... 128/305, 351, 305.1, 128/132

[56] References Cited

UNITED STATES PATENTS

| | | | |
|---|---|---|---|
| 3,467,098 | 9/1969 | Ayres | 128/305 R X |
| 3,618,611 | 11/1971 | Urban | 128/305 |
| 3,732,858 | 5/1973 | Banko | 128/305 X |
| 3,811,442 | 5/1974 | Maroth | 128/305 X |
| 3,867,943 | 2/1975 | Nordin | 128/305.1 |
| 3,902,500 | 9/1975 | Dryden | 128/351 |
| 3,906,954 | 9/1975 | Baehr et al. | 128/305 |

*Primary Examiner*—Channing L. Pace
*Attorney, Agent, or Firm*—Gipple & Hale

[57] ABSTRACT

A surgical instrument comprising a housing with a motor and source of power contained in the housing. A removable sheath is placed over the housing and a cutter assembly is removably mounted to the housing so that the housing is protected from external materials and contamination. The cutter assembly has a body, a tube projecting from the body, a blade positioned in the tube and a drive transfer mechanism mounted in the cutter body, connecting the blade to the motor. The tube defines an aperture and the blade in combination with the walls defining the aperture shears tissue entering the hole. A second passage is formed in the cutter body communicating with the tube to allow pressure differentials to be exerted to the tube.

18 Claims, 14 Drawing Figures

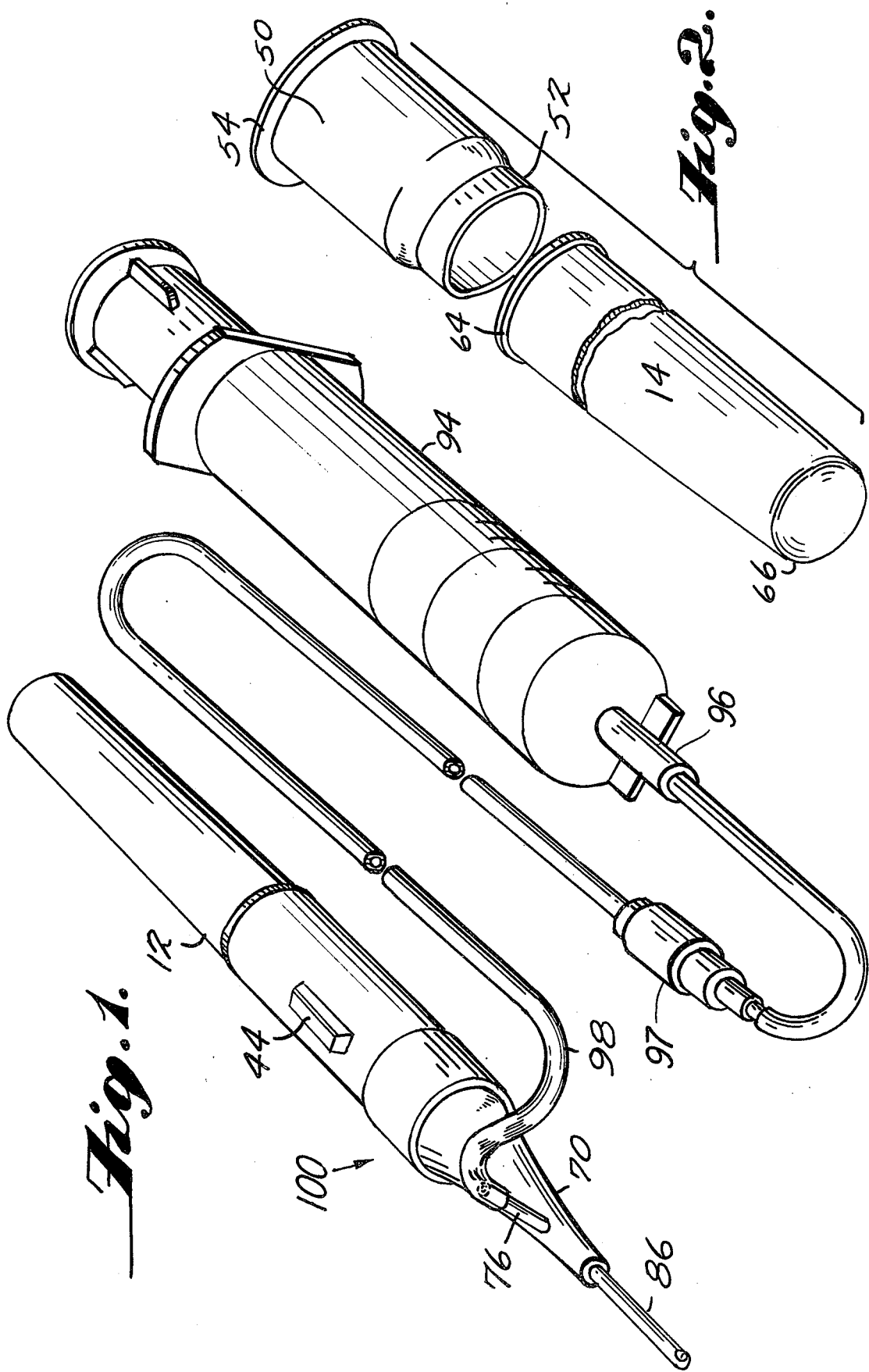

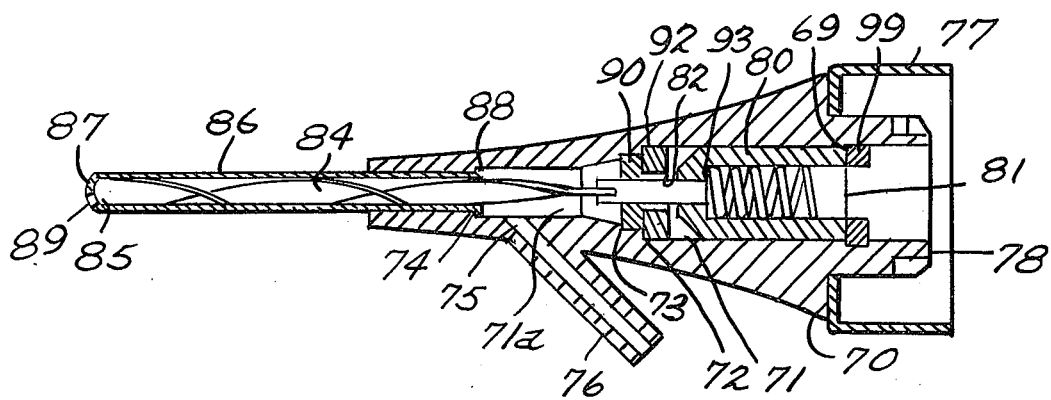
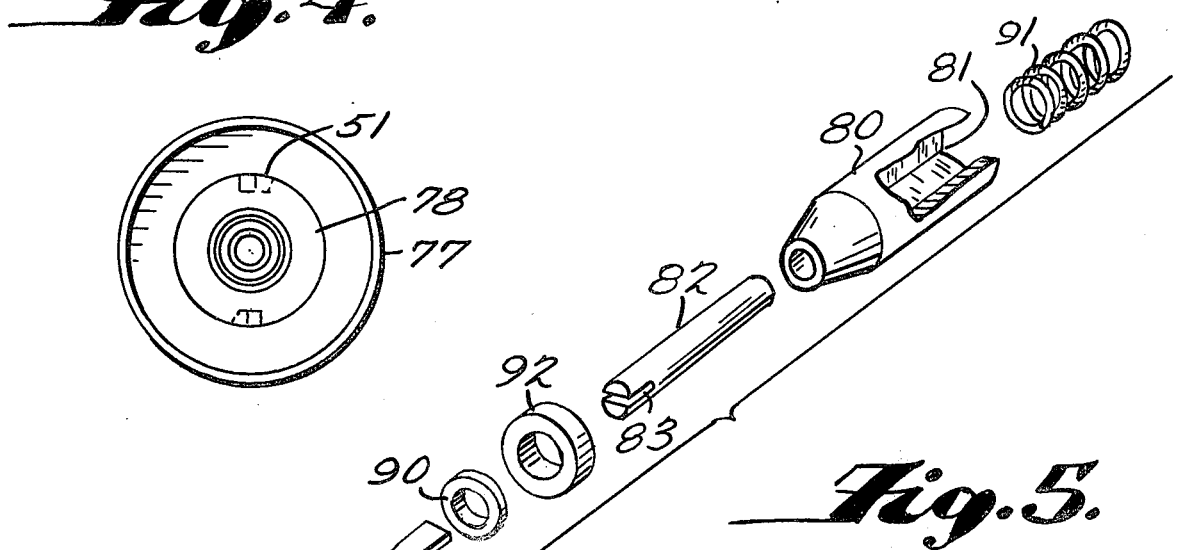
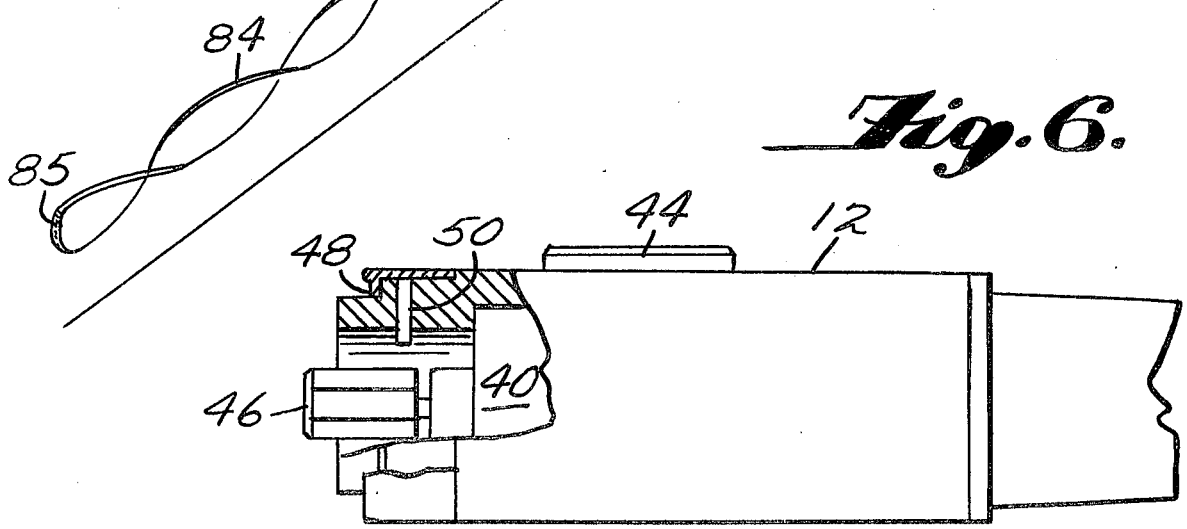

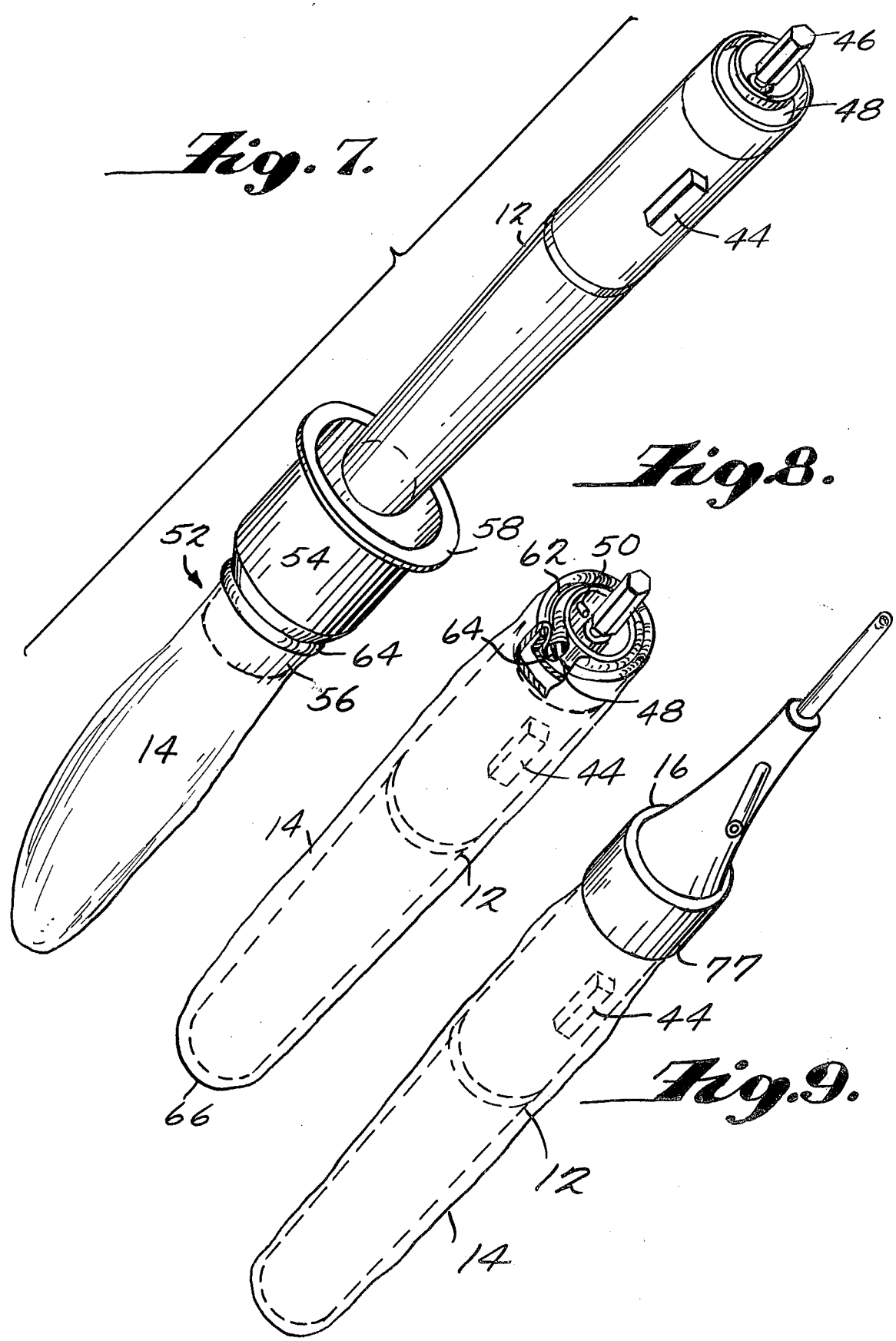

Fig. 10.
Fig. 11.
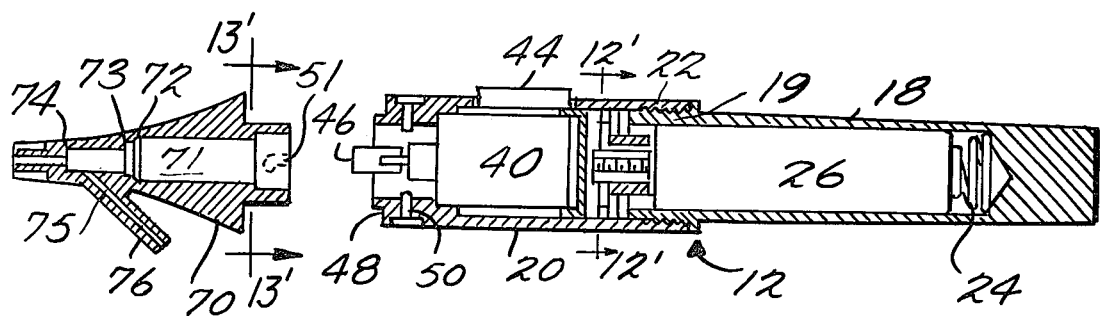
Fig. 12.
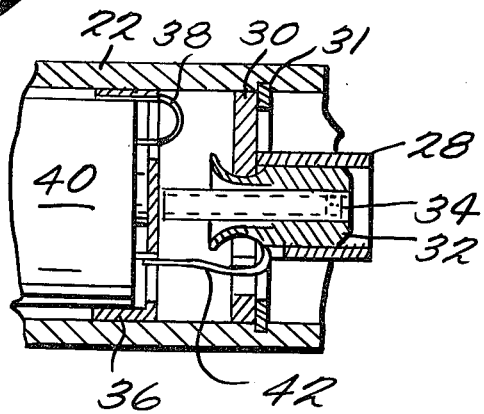
Fig. 13.
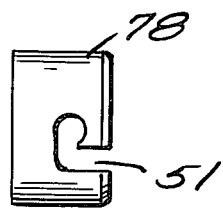
Fig. 14.
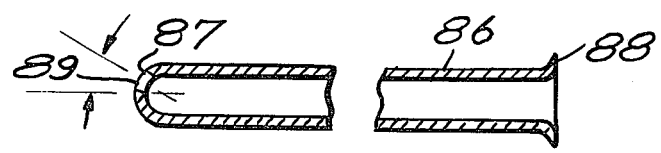

VITREOUS CUTTER

BACKGROUND OF THE INVENTION

The present invention relates to a powered surgical cutter and more particularly to a sterile disposable powered surgical cutter particularly adapted to perform eye surgery by cutting and removing vitreous from inside the anterior aqueous chamber of the eye.

A history of the development of such cutting devices is described in the AORN Journal, November 1973, Vol. 18, No. 5 page 908 in a article entitled Pars Plana Vitrectomy, a New Treatment for Vitreous Disease.

Eye surgery for management of vitreous in the anterior chamber after cataract extraction or in corneal surgery has been accomplished by several methods. Such methods have included sweeping of the vitreous from a wound with a spatula, aspiration of liquid vitreous through the pupil with a glass syringe and 18 gauge needle, aspiration of vitreous via the pars plana before opening the anterior chamber and removing vitreous directly from the anterior chamber with cellulose sponges and blunt scissors. The problems inherent in such techniques and methods and apparatus are disclosed in the Annals of Ophthalmology, September 1974, page 947 in an article, entitled Anterior Vitrectomy in Cataract Surgery, Aphakic Keratoplasty and Patients with Vitreous Pathology Using a Simple Vitreophage, and in the American Journal of Ophthalmology, June 1974, page 824, in an article entitled Companied Ketratoplasty and Cateract Extraction. In accomplishing eye surgery in the anterior aqueous chamber it has been found that after the incision is made it is sometimes necessary to draw off vitreous or in turn add vitreous fluid. Apparatus for accomplishing these ends is discussed in both of the above-mentioned periodicals. This initial apparatus was developed by Herbert E. Kaufman and incorporated various components and concepts that were well known in the art as is disclosed by the following patent references.

U.S. Pat. No. 3,734,099 discloses a hand held powered surgical cutter utilizing a cutter tip having an outer fixed tubular cutter in which an inner tubular cutter is rotated. The cutter tip is inserted into the eye and the inner cutter is rotated cutting the vitreous. The pieces of the severed vitreous are then removed through the interior of the inner tubular cutter to a disposal means. U.S. Pat. No. 3,618,861 discloses another similar hand held tubular cutting apparatus adapted to cut the vitreous in the eye and suck the cut vitreous to disposal means.

The use of ultrasonic energy in a surgical instrument to cut the vitreous is taught by U.S. Pat. No. 3,805,787. The apparatus has a probe head with bores cut therein to receive both suction means adapted to remove material emulsified by the probe and fluid transfer means to transmit irrigation fluid into the eye.

Another hand held vitreous cutter is disclosed in U.S. Pat. No. 3,732,858 which utilizes a rotating blade mounted in a tube to cut the vitreous material. As the vitreous is cut suction means draws the vitreous material back up through the tube housing of the cutting blade to an area for disposal. The apparatus is also shown in another embodiment adapted to be used with infusion means for submitting or directing fluid into the eye. The present invention represents an improvement over this previously identified prior art.

All of the previously disclosed apparatus must be sterilized after each operation. A common sterilization technique in hospitals is to sterilize the units with ethylene oxide. The construction of the apparatus is such that the cutter blade assembly which is hardest to sterilize, is difficult to reach in sterilizing processes, expensive to manufacture and is constructed to form a complex cutter assembly. Furthermore the drive mechanism of the cutters blade assembly has to be sterilized after each use resulting in damage to the mechanism after repeated sterilization not to mention the time, labor and expense required for each sterilization.

The present invention is thus constructed with a simple disposable cutter assembly which can be either disposed of or sterilized while another cutter assembly is placed on the drive housing. The novel use of a removable protective bag which is sealed by the disposable cutter assembly to the drive housing prevents the drive housing from being contaminated so that the drive housing can be reused within minutes or within a minute after its use in the previous operation. Because of the self contained power source the instrument can be used in the field or in other remote places where power is not available. Thus the invention provides a sophisticated low cost sterile medical instrument available for use under any environment or condition.

SUMMARY OF THE INVENTION

The surgical cutter of the present invention is an improvement over apparatus and methods previously disclosed in the prior art and comprises a drive housing having motor means and a power source mounted in the drive housing. An elongated external removable cutter assembly is attached to one end of the housing. The external cutter assembly comprises an outer housing mounted to the drive housing, a drive transfer assembly mounted in the outer housing, a closed end tubular blade housing secured to the outer housing and a rotatable blade, which is urged forward in the tubular blade housing by a spring construction, to abut against the closed end of the tubular blade housing of the drive transfer assembly. The rotation of the blade within the tubular blade housing will shear off tissue drawn into an opening formed in the end of the tubular blade housing and when used with suction provided by a syringe or other suitable suction means the cut material will be drawn through the interior of the cutter tip assembly into a suitable depository. A protective sheath is adapted to fit over the drive housing into a channel formed on the end of the drive housing so that it engages the cutter assembly to form a fluid seal. The cutter assembly outer housing preferably has an end skirt construction which fits over the motor end of the drive housing and its associated sheath to protect the drive housing.

Although the invention will be set forth in the claims the invention itself and the manner in which it may be made and used, may be better understood by referring to the following description taken in connection with the accompanying drawings forming a part hereof in which like reference numerals refer to like parts throughout the several views and in which:

FIG. 1 is a perspective view showing the powered surgical cutter of the present invention;

FIG. 2 is a perspective view of the disposable sterile sheath assembly used with the powered surgical cutter;

FIG. 3 is a cross-sectional view of the disposable cutter head of the invention shown in FIG. 1;

FIG. 4 is an end view of the disposable cutter head shown in FIG. 3;

FIG. 5 is an exploded perspective view partially in cross section of the blade and blade drive assembly shown in FIG. 3;

FIG. 6 is a side view of the motor end of the drive housing partially in section;

FIG. 7 is a perspective view of the invention showing the instrument drive housing about to be placed in a sterile surgical receptacle;

FIG. 8 discloses the instrument of FIG. 7 inside the sterile sheath with the end of the instrument and sheath partially shown in cross section to show the relation of the instrument with the sheath;

FIG. 9 discloses the instrument with the cutter head placed on the sheath and drive housing when locked into position;

FIG. 10 discloses a cross sectional view of the cutter head housing;

FIG. 11 shows a cross sectional view of the drive housing;

FIG. 12 discloses a partial enlarged cross sectional view of FIG. 11 taken along lines 12' — 12';

FIG. 13 discloses an enlarged side view of the end of the cutter head housing taken along lines 13' — 13' of FIG. 10; and FIG. 14 shows an enlarged cross sectional view of the blade housing tube of the cutter head assembly.

DESCRIPTION OF THE PREFERRED EMBODIMENT

Referring now to the drawings the disposable surgical cutting instrument 100 of the present invention has a drive housing 12 of generally cylindrical form designed to be easily held in the surgeons hand.

It should be noted at the outset that all parts of the invention which could possibly come in contact with the patient during an operation are sterilized and pyrogen free.

A protective latex sheath 14 is adapted to be placed over the drive housing to protect the drive housing from contamination when the operation is performed. A disposable cutting head 16 is mounted on the drive housing 12 in engagement with the sheath 14. The disposable cutting head is driven by a drive shaft of a micro motor mounted in the drive housing so that only the cutting head 16 and sheath 14 comes into contact with blood, vitreous and other materials during the operation.

The drive housing 12 as shown in FIGS. 6–9, 11 and 12 is constructed of two components comprising a power source section 18 and a motor section 20. The power source section 18 has one end provided with an outer threaded surface 19 which is adapted to be screwed into a threaded inner surface 22 of the motor section to form the complete drive housing 12. A free seated coiled spring 24 is seated in one end of the power source section 18 and abuts against a battery 26 which is slidably mounted in the housing for easy replacement to urge the battery toward a standoff sleeve 28. The battery does not engage the standoff sleeve. The sleeve merely prevents electrical contact in case the battery is inadvertently installed backward. The standoff sleeve 28 is secured to a bulkhead 30 by cement means or press fit on the conductor. One end of the battery is engaged with a modified rivet contact 32 that is riveted in place. The bulkhead 30 is positioned within the motor housing section by a retaining ring 31 which is mounted in a channel cut in the housing. The set screw 34 contacts a motor support 36 mounted to the housing and holds the motor in place. A stripped wire 38 is bent and squeezed between the micromotor 40 and motor support 36 to form a connection. The micromotor 40 is mounted in the motor housing and is electrically connected to the contact 32 by wire 42 so that when switch 44 is depressed an electrical contact is made between the battery and the micromotor energizing the micromotor 40 to drive a hexagonal shaped drive shaft 46 of the micromotor. It should be noted that while the preferred embodiment discloses a hexagonal drive shaft 46, the drive shaft could be square, flat or shaped in any other manner. The drive shaft end of the motor section forms a seat or channel 48 depending upon its construction and has two locking pins 50 protruding inwardly from the collar to fit bayonet slots 51 formed in the disposable cutting head 16. The drive housing is covered by using a sheath assembly 52 comprising a sleeve 54 having a tapered end 56 upon which the latex sheath 14 is stretched and mounted. The other end 58 of sleeve 54 is open and flanged outward so that the drive housing can be easily inserted into the mounted sheath.

The flexible latex sheath 14 has an open end 62 formed with a lip 64 which fits into the seat 48 defined in the motor section of the drive housing. The other end 66 of sheath 14 is closed. After the drive housing 12 has been deposited into the protective covering of the latex sheath the sleeve 54 is removed and lip 64 is inserted into the seat 48 formed in the end of the housing. The cutter head 16 is constructed with a body 70 having a varying diameter axial bore 71 cut therethrough. The bore 71 is cut in a series of steps so that the diameter narrows after each step. The steps form shoulders 69, 72, 73 and 74 which are adapted to respectively receive retainer ring 99, retainer ring 92, "O" ring 90 and flange 89.

The cutter body 70 is provided with a second bore 75 and a tubular extension 76 axially aligned with the bore allowing a suction or irrigation device to communicate with bore 71. Thus a syringe can be connected to the tubular extension 76 by a hose to provide suction to a chamber portion 71 a and the interior of tube 86 so that material severed by blade 84 travels through the tube into chamber portion 71 a past bore 75 into a suitable disposal means such as the syringe. Alternatively a saline solution or other suitable fluid can travel the same path through the tube 86 to the eye.

The body 70 has a generally tapered exterior surface and is cut at one end in an annular manner to receive a skirt 77 which is cemented to the annularly cut end of the body. The outer surface of the annularly cut end or tip 78 is provided with two bayonet slots 51. When the tip 78 is inserted into the motor section, the tip 78 fits around the hexagonal drive shaft 46 of the micromotor with the skirt 77 projecting over the outer surface of the motor section and the latex sheath 14.

A clear plastic coupling member 80 is mounted in the cutter body bore 71. The coupling member 80 has an axial bore 81 with a circular configuration at one end suitable to hold a coupling member drive shaft 82 and a suitably shaped configuration at the other end to slidably receive and hold the drive shaft 46. In the preferred embodiment a coiled spring member 91 is seated in the hexagonal portion of the bore 81 and abuts against shoulder 93 which forms the end of the hexagonal portion of bore 81. When the hexagonal drive shaft 46 is inserted into the hexagonal portion of the bore 81 the coupling member 80 is urged forward by spring member 91 to place blade 84 against the end of the tube housing 86. The drive shaft 82 is notched at 83 to freely hold the blade 84. In this preferred embodiment the blade 84 is freely mounted in notch 83 and is not secured to the drive shaft 82. An external fixed thin walled tube 86 projects from the end of the body 70 with the distal end 87 being formed into a hemisphere closing it off. The proximal end 88 is opened and flanged outwardly so that it is seated on a first shoulder 74 in the interior of body 70. The flanged end 88 is press fit to the shoulder or stop but it can be cemented if desired. A small cutting hole 89 is located in the distal end of the tube preferably positioned 180° from the hose nozzle or projection 76. The blade 84 is preferably twisted into at least two revolutions with one end being flat so that it can be seated in the notch 83 cut in the end of drive shaft 82 with its distal end 85 being rounded so that it can easily rotate in the hemispherical shaped end 87 of the tube 86. If desired a flat blade can be substituted for the twisted blade. In the twisted construction the blade is continuously urged forward against end 87 by spring means 91. The blade is smaller in width than the inner diameter of tube 86 so as to just fit inside tube 86 and still be free to rotate. The rotation of the blade helps drive the severed material back through the tube 86.

A clear plastic seal retainer ring 92 and O ring 90 are mounted around the coupling member drive shaft 82 to keep fluids from entering into the cavity housing the coupling means, thus preventing any leakage of vitreous material, fluid, blood or other materials past the shaft. The O ring seal also prevents air from being drawn into the syringe via motor shaft leakage. The shaft 82 and O ring 90 effectively seal off bore 71 to form a fluid receiving chamber 71 a.

A syringe 94 is connected to the hose nozzle 76 by flexible tubing 98 which is inserted over the hose nozzle or projection 76 on one end and onto a female luer-lok 96 in the syringe. Thus suction or fluid can be transmitted to tube 86.

In the operation and before the actual cutting of the vitreous is to take place, the surgeon takes the drive housing 12, drops it into the sleeve 54 made of a suitable material into an associated sheath 14. The sheath lip 64 is inserted into the seat 48 of the drive housing and the disposable plastic cutter head 16 is mounted on to the housing so that bayonet slots 51 cut into the cutter head are mounted over the pins 50 of the motor section with the cutter head then being depressed and turned so that it is locked into place on pins 50. Simultaneously its outer skirt 77 extends down over the drive housing which is covered by flexible sheath 14. The lip 64 in combination with the drive housing and cutter head forms a fluid tight seal so that any fluid that might enter under skirt 77 is prevented from contacting the motor housing by sheath 14. The syringe 94 is then connected to the cutter hose nozzle 76 so that suction can be applied. A check valve 97 is mounted in the flexible tubing 98 to prevent the introduction of fluid into the eye. When the opening is made in the anterior aqueous chamber the cutter tube 86 is inserted in the chamber. The surgeon depresses the switch 44 of the micro motor 40 through the protective sheath 14 activating the motor and thereby rotating the blade 84 within the tube 86. The blade 84 is constantly urged forward by the coupling member 80 through spring means 91 in the coupling member so that the blade edge 85 is pressed against the front of the tube and rotates over hole 89 cut in the end of the tube. As suction is applied to the instrument vitreous material is drawn into the hole. The rapidly rotating spring loaded blade 84 which fits flush against the hole 89 severs the vitreous carrying it into the tube with the construction of the blade 84 being such that it is carried into chamber 71 a of the cutter head and from there into a syringe or other suitable material disposal means.

The cutter of the present invention, although specifically designed for eye surgery could also be used to remove any other body tissue in the same manner. Because of the sealed nature of the internal structure of the tip, foreign materials cannot proceed past the blade drive shaft or chamber 71a so that no foreign materials contact the hexagonal drive shaft or interior of the drive housing. After the operation has been completed the surgeon rotates the cutter head releasing it from its bayonet connection and removes the head from the drive housing. The head is then thrown away or sterilized for future reuse and the latex protective sheath 14 is removed from the drive housing so that the drive housing is ready for the next operation. When the next operation is ready to begin a new disposable cutter head and a new disposable sheath are placed on the instrument as previously indicated so that no problem of sterilizing the instrument is incurred with the instrument being maintained in a sterile condition.

In the foregoing description the invention has been described with reference to a particular preferred embodiment although it is to be understood that the specific details shown are merely illustrative and that the invention may be carried out in other ways without the departing from the true spirit and scope of the following appended claims.

What is claimed is:

1. A surgical instrument comprising a housing, motor means mounted in said housing and contained in said housing, said motor means being connected to a source of power, a removable sheath means mounted over said housing and surrounding said housing to protect said housing from external materials and contamination, said sheath means defining annular lip means which is securely held between a cutter means and said housing to prevent contamination materials from entering said sheath means, said cutter means removably mounted to said housing, said cutter means comprising a body, a tube projecting from said body, a blade means positioned in said tube and drive transfer means mounted in said cutter means body, said drive transfer means connecting said blade means to said motor means for movement of said blade means when said motor means is activated, said tube defining an aperture, said blade means in combination with the walls defining said aperture being adapted to shear tissue entering said hole and a passage means formed in said cutter body and communicating with said tube to allow pressure differentials to be exerted to said tube.

2. A surgical instrument as claimed in claim 1 wherein said cutter means includes a skirt which extends over said sheath lip means and said removable sheath means.

3. A cutter means as claimed in claim 1 wherein said cutter body is disposable.

4. A surgical instrument as claimed in claim 1 wherein said source of power is battery means located within said housing.

5. A cutter means as claimed in claim 1 wherein said drive transfer means comprises a drive shaft removably connected to said blade means, a coupling member secured to said drive shaft, spring means mounted in said coupling member adopted to urge said blade means away from said drive housing when a drive shaft of the motor means engages said coupling member.

6. The drive transfer means of claim 5 further comprising seal means surrounding said drive shaft and engaging said cutter body to maintain a fluid tight seal between said coupling member and said cutter blade.

7. The apparatus of claim 6 wherein said seal means is an O ring.

8. The surgical instrument as claimed in claim 1 further including a source of vacuum connected to said cutter body passageway, said source of vacuum comprising a syringe connected to said passageway by a hose means, said syringe being adapted to be activated by pulling the plunger out of the syringe to form a partial vacuum in the syringe and in the passageway leading out to the hole formed in said tube.

9. A surgical cutting apparatus comprising a drive housing, sheath means surrounding said drive housing and mounted to said drive housing, a removable cutting means mounted to said drive housing in engagement with said sheath means to form a fluid tight seal between said drive housing, sheath means and removable cutting means, motor means mounted in said drive housing, said motor means including a micromotor with a drive shaft, a source of power mounted in said drive housing, said motor means and source of power being enclosed in said drive housing, said removable cutting means comprising a transfer means adapted to be connected to said motor shaft and blade means connected to said transfer means and adapted to be driven by said transfer means when said motor means is energized.

10. A surgical cutting apparatus as claimed in claim 9 wherein said cutting means comprises a body defining an axial bore, transfer means slidably mounted in said bore, said transfer means comprising a coupling member, a shaft secured to one end of said coupling member, the other end of said coupling member being formed to receive said micromotor drive shaft, seal means surrounding said coupling member shaft dividing said axial bore into at least separate implartments, a tube secured to said body in axial alignment with said bore and a blade mounted on said coupling member shaft positioned in said tube.

11. A surgical cutting instrument as claimed in claim 9 wherein said sheath means comprises a flexible pack having a closed end and an open end with an annular lip.

12. A surgical cutting instrument as claimed in claim 11 wherein said sheath means is latex.

13. A surgical cutting instrument as claimed in claim 9 wherein said cutting means includes a pressure change means connected therewith adapted to change the pressure around said blade means.

14. A surgical instrument as claimed in claim 1 wherein said sheath means is latex.

15. A surgical instrument as claimed in claim 1 wherein said annular lip means of said sheath is held within an annular channel formed in said housing in a fluid tight seal between said housing, sheath means and cutter means.

16. A surgical cutting device comprising a housing, motor means mounted inside said housing, means to energize said motor means mounted inside said housing, a disposable cutter head removably secured to said housing, said disposable cutter head comprising a body, an elongated tube secured to said cutter head body, a blade positioned in said tube and adapted to rotate within said tube, said tube being provided with an aperture therein to allow said blade to come in contact with tissue, drive transfer means mounted in said disposable cutter head, said drive transfer means being adapted to engage said motor means and said blade to transmit motion from said motor means to said blade, said disposable cutter head defining a passage-way communicating with said tube adapted to supply a vacuum from a source to said tube so that tissue sheared off by the rotation of said blade inside said tube will be carried off into said passage-way, and a removable sheath mounted over and held against said housing by said disposable cutter head to protect and keep said housing from contamination, said sheath having an annular lip which seats in a channel formed in said housing, said sheath providing a fluid tight seal between said housing, sheath and disposable cutter head keeping said housing in uncontaminated condition for immediate reuse.

17. A surgical instrument as claimed in claim 16 wherein said blade has a flat linear body twisted into at least two revolutions.

18. A surgical instrument as claimed in claim 17 wherein said blade has a rounded end and said tube end provided with an aperture has a hemispherically shaped end.

* * * * *